United States Patent [19]
Reuben

[11] Patent Number: 5,448,489
[45] Date of Patent: * Sep. 5, 1995

[54] PROCESS FOR MAKING CUSTOM JOINT REPLACEMENTS

[75] Inventor: Jeffrey D. Reuben, Houston, Tex.

[73] Assignee: Board of Regents, The University of Texas System, Austin, Tex.

[*] Notice: The portion of the term of this patent subsequent to Dec. 28, 2010 has been disclaimed.

[21] Appl. No.: 143,353

[22] Filed: Oct. 26, 1993

Related U.S. Application Data

[63] Continuation of Ser. No. 592,547, Oct. 3, 1990, Pat. No. 5,224,265.

[51] Int. Cl.⁶ ............................................. G05B 19/18
[52] U.S. Cl. .................... 364/474.05; 364/468; 364/413.15; 364/474.24
[58] Field of Search ............... 364/474.24, 474.05, 364/468, 413.15–413.22; 623/16, 20, 22, 23, 66, 18

[56] References Cited

U.S. PATENT DOCUMENTS

| | | | |
|---|---|---|---|
| 3,778,614 | 12/1973 | Hounsfield | 250/364 |
| 3,881,110 | 4/1975 | Hounsfield | 250/360 |
| 3,945,053 | 3/1976 | Hillberry et al. | 3/1.911 |
| 4,135,247 | 1/1979 | Gordon et al. | 364/414 |
| 4,436,684 | 3/1984 | White | 264/138 |
| 4,538,227 | 8/1985 | Toraichi et al. | 364/414 |
| 4,704,686 | 11/1987 | Aldinger | 364/468 |
| 4,822,365 | 4/1989 | Walker et al. | 364/468 |
| 4,853,970 | 8/1989 | Ott et al. | 382/54 |
| 4,872,187 | 10/1989 | Nakahata et al. | 378/4 |
| 4,873,707 | 10/1989 | Robertson | 378/18 |
| 4,936,862 | 6/1990 | Walker et al. | 364/468 |
| 5,274,565 | 12/1993 | Reuben | 364/474.24 |

FOREIGN PATENT DOCUMENTS

| | | |
|---|---|---|
| 0093869A1 | 11/1983 | European Pat. Off. . |
| 0097001A1 | 12/1983 | European Pat. Off. . |
| 0255797A1 | 2/1988 | European Pat. Off. . |
| 2577697 | 6/1986 | France . |
| 3522196A1 | 2/1986 | Germany . |

OTHER PUBLICATIONS

Biomedizinische Technik, vol. 30, No. 5, 1 May 1985, Berlin de pp. 111–114; Giebel, et al. "Fertigung von Knochenmodellen nach Computer-Tomographie Daten zur Verwendung in Chirurgie und Orthopadie".

Electro Medica (Siemens), vol. 56, No. 1, 1988, Erlangen de pp. 24–29; Robertson, et al. "Anspruchsvolle CT-Bildgebungsverfahren: Anwendungen in der Orthopadischen Chirurgie der Hufte".

Artzy et al., *Computer Graphics and Image Processing*, 15, pp. 1–24 (1981).

Chou et al., *Journal of Nuclear Medicine*, Proceedings of the 35th Annual Meeting, p. 868, Abstract No. 526. date unknown.

Goldberg et al., *Diseases of the Nervous System II*, p. 499, Abstract No. 138.11. date unknown.

Granholm et al., *IEEE CG & A*, pp. 26–35 (Feb. 1987).

Rhodes et al., *Proceedings of the 6th Annual Conference*

(List continued on next page.)

*Primary Examiner*—James P. Trammell
*Attorney, Agent, or Firm*—Marshall, O'Toole, Gerstein, Murray & Borun

[57] ABSTRACT

A process for forming a prosthesis related to bone structure internal to a body using CT scan data corresponding to the radiological density of the bone structure to derive the inner and outer bone surface contours. The density and the density gradient of discrete points in the bone structure compared to threshold density levels and to threshold density gradient levels and points are selected to form a series of interim outer contours. A contour shape factor is derived for each interim outer contour, and that interim contour is chosen in which the contour shape factor is maximum denoting less fluctuations in the contour circumference. The bone surface contour data is used to develop a graphic model from which a set of digital data is generated for a surface model representing the graphic model. A set of numerical control machine instructions are generated to make the prosthesis.

1 Claim, 6 Drawing Sheets

OTHER PUBLICATIONS

*and Exposition of the National Computer Graphics Association*, pp. 110–124 (1985).

Robertson et al., *Medical Physics*, 13:4, pp. 474–479 (Jul./Aug. 1986).

Robertson, *Journal of Computer Assisted Tomography*, 11:5, pp. 804–809 (Sep./Oct. 1987).

Rothman et al., *Radiology*, 157, p. 177, Abstract No. 448 (1985).

Seitz et al., *IEEE Transactions on Medical Imaging*, MI-2:3, pp. 136–141 (Sep. 1983).

Ter–Pogossian, *Seminars in Roentgenology*, 12:1, pp. 13–25 (Jan. 1977).

Williams et al., *Investigative Radiology*, 24:10; pp. 768–775 (Oct. 1989).

Woolson, *Clinical Orthopaedics and Related Research*, No. 202, pp. 239–248 (Jan. 1986).

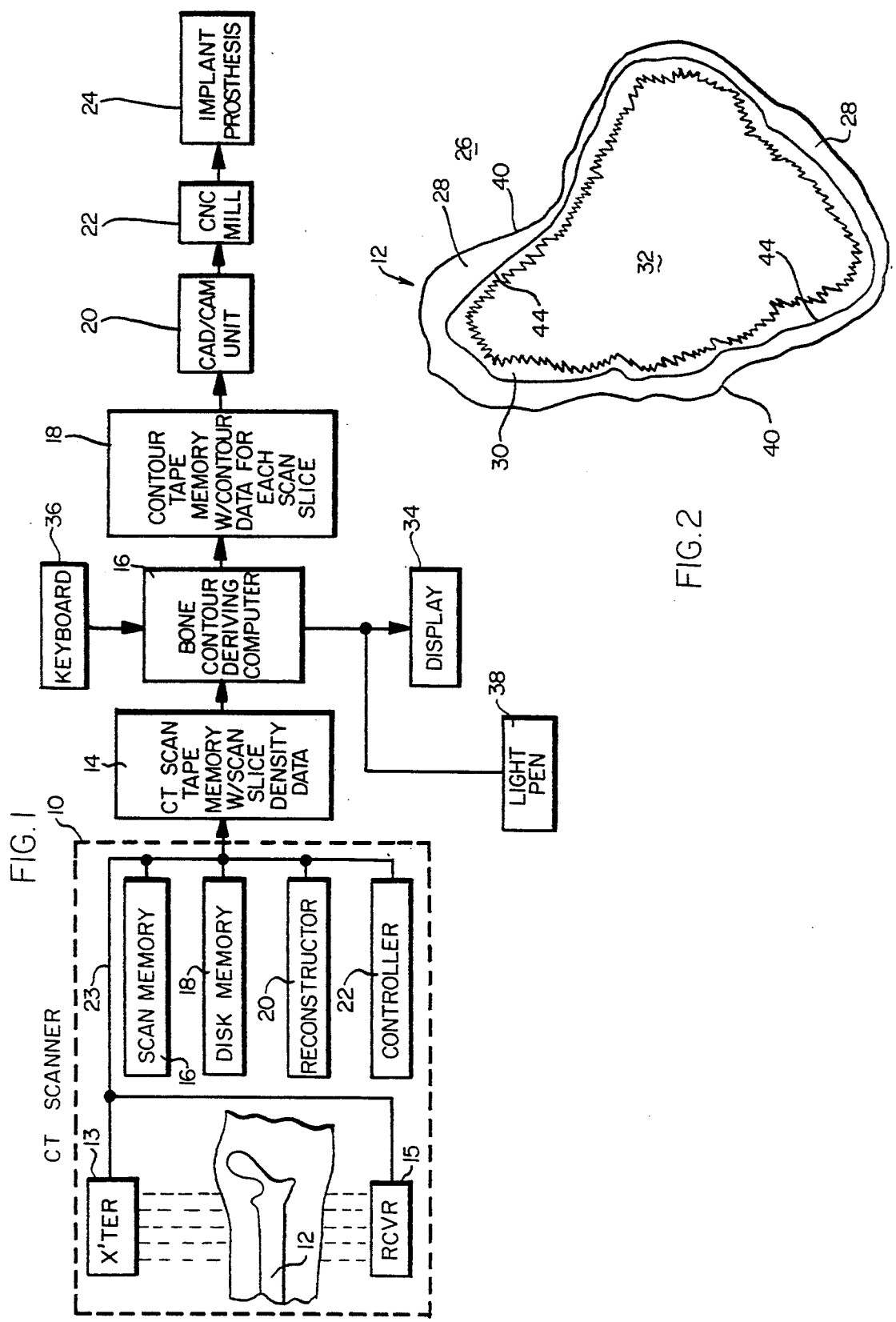

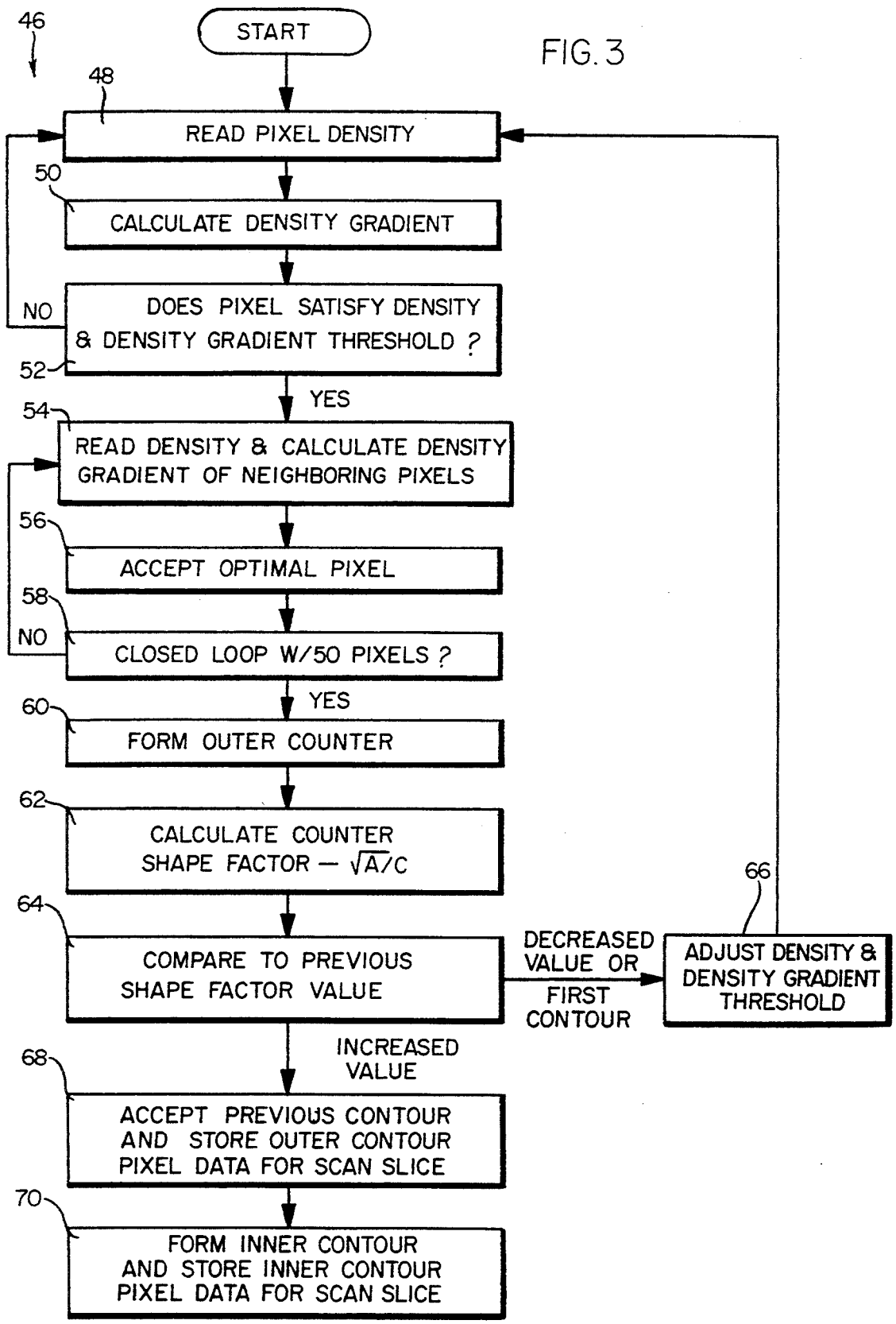

OUTER CONTOUR ROUTINE
W/ SHAPE FACTOR ROUTINE

INNER CONTOUR ROUTINE

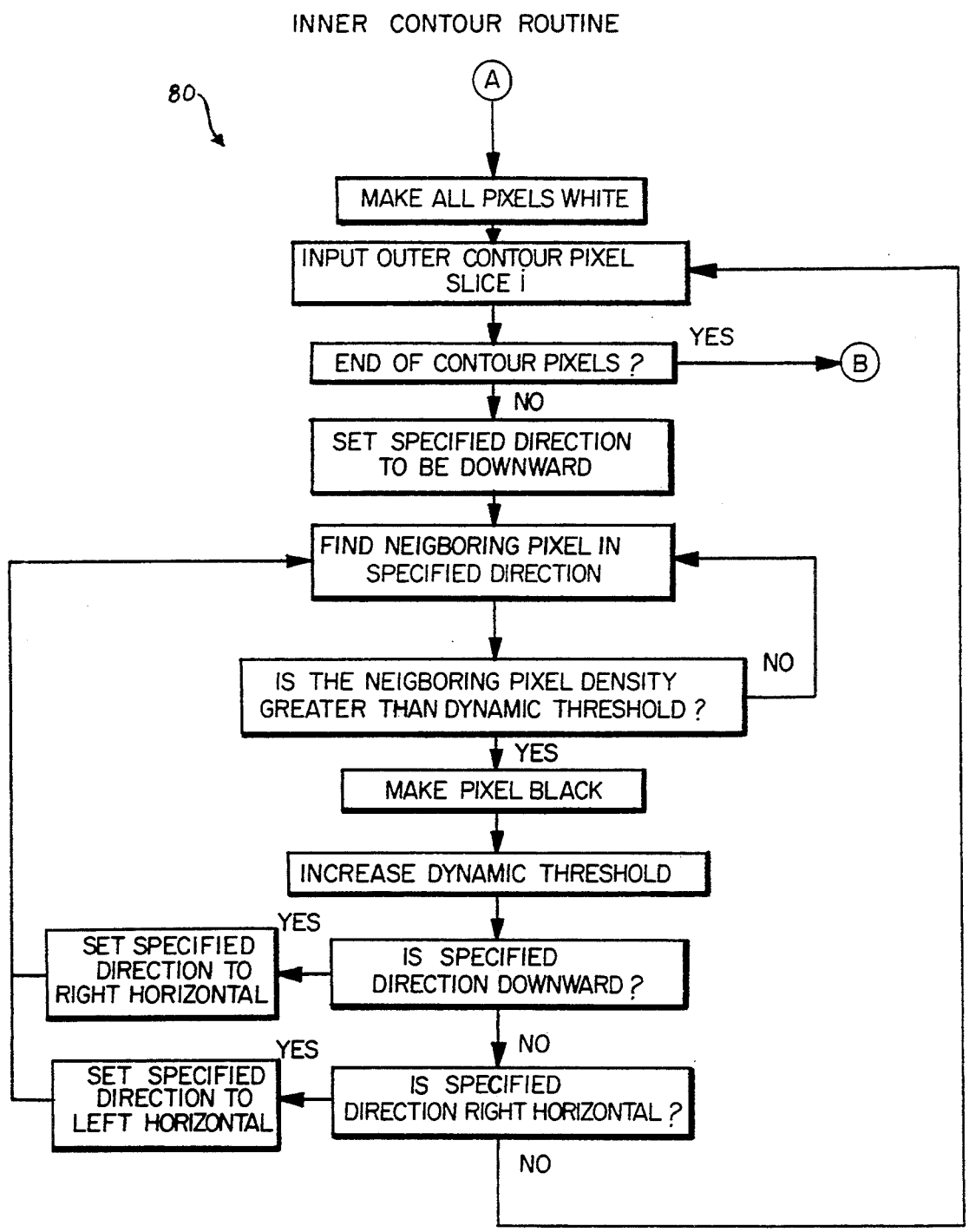

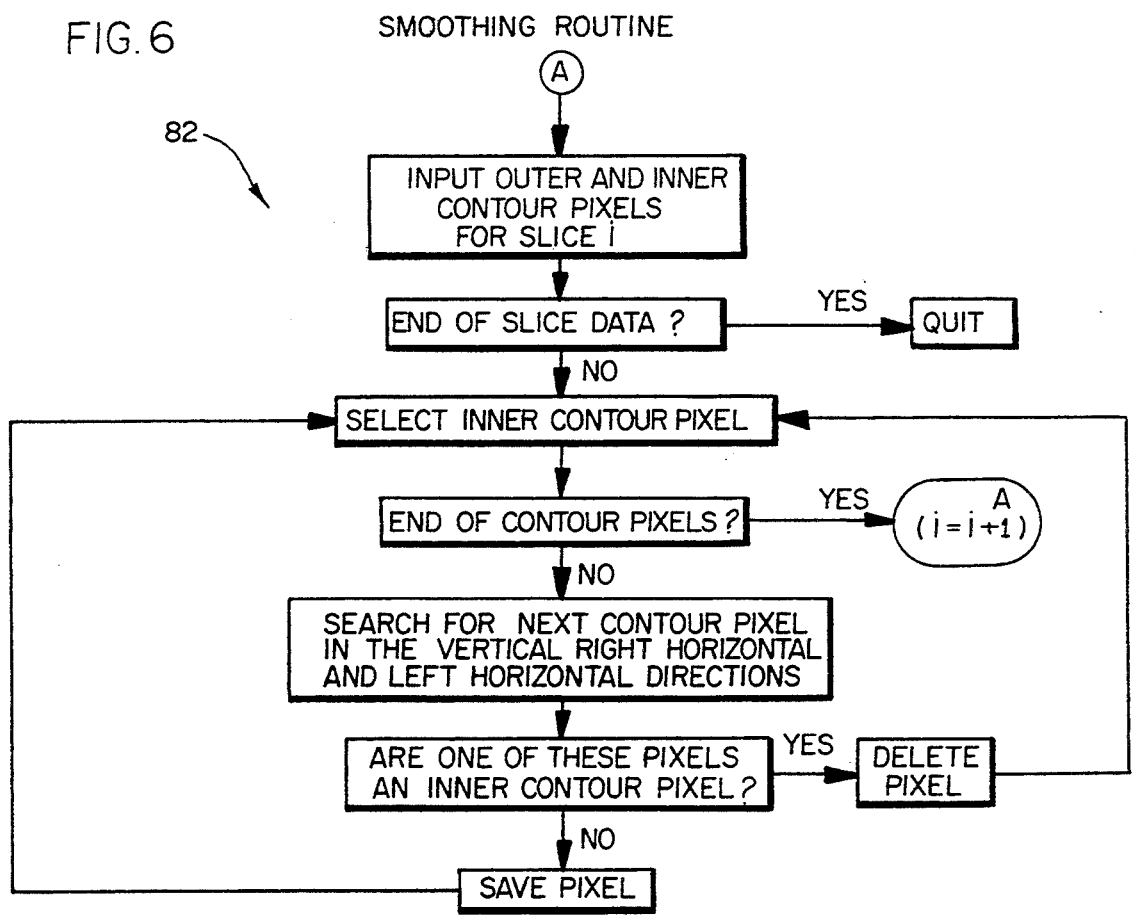

PROCESS FOR MAKING CUSTOM JOINT REPLACEMENTS

This is a Continuation of U.S. application Ser. No. 07/592,547, filed Oct. 3, 1990, now U.S. Pat. No. 5,274,269.

This invention relates to a process for making custom replacements, and in particular to a process for designing such a total joint replacement from information pertaining to a particular patient with significantly less errors in matching the individual's joint geometry.

BACKGROUND OF THE INVENTION

The requirement for total joint replacement has increased significantly due in large part to the increasing age of the general population in which arthritic joints become more prevalent, and due to the increased physical activities of the general population. In response to this need, many advances in the field of total joint replacement, such as knees, hips, elbows, have been realized. Complication and failure rates have been markedly reduced, the quality of implant materials have been improved, and the indications for surgery have been refined. In spite of these advances however, total joint replacement has not been successful in the young, high demand or overweight patient.

The reason for this lack of success is because typically the prosthetic replacement is a selection of one size out of several available sizes. Secondly, where proposals have been made or attempted in the past involving a custom joint replacement, obvious shortcomings are apparent in the mismatch of the prosthetic replacement with the patient's joint geometry.

Presently, the usual procedure in total joint replacement is one in which the clinician selects the most suitable prosthesis for a given patient from a fairly large variety of commercially available prosthetic designs.

Most manufacturers of total joint replacements have based their designs on the replication of normal joint anatomy. However, the selection and attempt to match a particular patient with one of the commercially available prosthetic designs is most difficult since joint geometry is unique for each individual.

Information on the individual's joint geometry is available through standard non-invasive techniques, such as radiological, magnetic resonance and nuclear examination and imaging techniques. Generally, such techniques involve developing a medical image of the joint in two dimensional representations from which measurements may be taken and if desired three dimensional models can be constructed.

Proposals have been made for advanced systems in which displayed data from a computerized tomographic device (CT) is analyzed to define the bone from the surrounding soft tissue. Generally, such advanced techniques require a technician to interact with the displayed CT scan image to intelligently speculate with respect to the threshold of certain values represented by the displayed image so that the system can thereafter form the boundary between bone and surrounding soft tissue. Typically, the threshold value relates to either a single threshold value of radiological density determined in the CT scan process, or to a threshold range of such density values. These enhanced systems still provide errors of about 8% when compared against hand measured values of subject joints.

Thus, while the newer, enhanced systems represent an earnest attempt to provide a better design of custom joint replacements compared to the selection and matching process presently in use, because of the large errors, custom joint replacements are still not a viable design alternative to the present standard selection and matching techniques. Accordingly, in current practice, the choice of a prosthetic replacement is usually made on the basis of which prosthetic design the attending physician is most comfortable using based on his past experience.

Accordingly, it is desirable to provide a process for making custom joint replacements which are unique to an individual's joint geometry and therefore with significantly less errors than with prior techniques so that the customized joint components will achieve a greater degree of implant reliability and function.

SUMMARY OF THE INVENTION

In accordance with the principles of the present invention, there is provided a process for making custom joint replacements which utilizes data from a CT scan device to provide a more accurate design prosthesis. Initially, data from a CT scan is reviewed both with respect to a certain threshold density value and with respect to the rate of change of the density when comparing an array of $512 \times 512$ elements or pixels that have an associated radiologic density (Houndsfield number). Next, a contour between the bone and surrounding soft tissue is formed by connecting selected pixels which meet the preselected criteria involving not only a threshold density value, but also the rate of change of the density between a particular pixel and its neighboring pixels, which rate of change exceeds a second threshold value. Next, an interim contour is formed.

Once the interim contour is formed, a contour shape factor is calculated which takes into account the area bounded by the interim contour and the circumference of the interim contour. It has been determined that when inappropriate density threshold values or density gradient threshold values are chosen, then the circumference of the contour will markedly decrease. Therefore, if a variety of density thresholds and density gradient thresholds are utilized and the resulting shape factor is calculated, then the computer can choose which combination of density threshold and density gradient threshold values are optimal based on the manner in which the shape factor value changes.

For example, it has been determined that if the calculated contour shape factor of the contour in question exceeds 0.2 or if three successive calculations of the contour shape factor result in a decreasing value, then the contour is chosen with the largest shape factor value.

Utilizing threshold density, and threshold density gradients as well as the aforementioned contour shape factor, a significantly improved accuracy in determining joint geometry has been obtained in accordance with the invention. As an example, compared to hand measurements of joint geometry and an about 8% average error attained by the most advanced of currently available systems, the present invention provides determinations of bone contour with average errors reduced to about 2%.

The inner contour is formed using the outer contour data and the density values. Once the outer and inner bone surface contour data is formed, development of a prosthesis is undertaken with conventional steps using a commercially available CAD CAM system such as McDonnell Douglas Unigraphics to generate numerical control machine instructions.

BRIEF DESCRIPTION OF THE DRAWINGS

The features of this invention which are believed to be novel are set forth with particularity in the appended claims. The invention may be best understood by reference to the following description taken in conjunction with the accompanying drawings, in which like reference numerals identify like elements in the several figures and in which:

FIG. 1 is a block diagram illustrating components useful in practicing the present invention;

FIG. 2 is an illustration of the cross section of a femur;

FIG. 3 is a flow chart illustrating the main computer program executed by the bone contour deriving computer of FIG. 1;

FIG. 5A is a flow chart illustrating an inner contour deriving routine utilized during the steps of the flow chart of FIG. 3;

FIG. 6 is a flow chart of an inner contour smoothing routine utilized during the steps of the flow chart of FIG. 3; and FIG. 7 illustrates a density lookup table utilized during the steps of the outer contour and shape factor routines of FIGS. 4A and 4B.

DETAILED DESCRIPTION

Figure 4A:
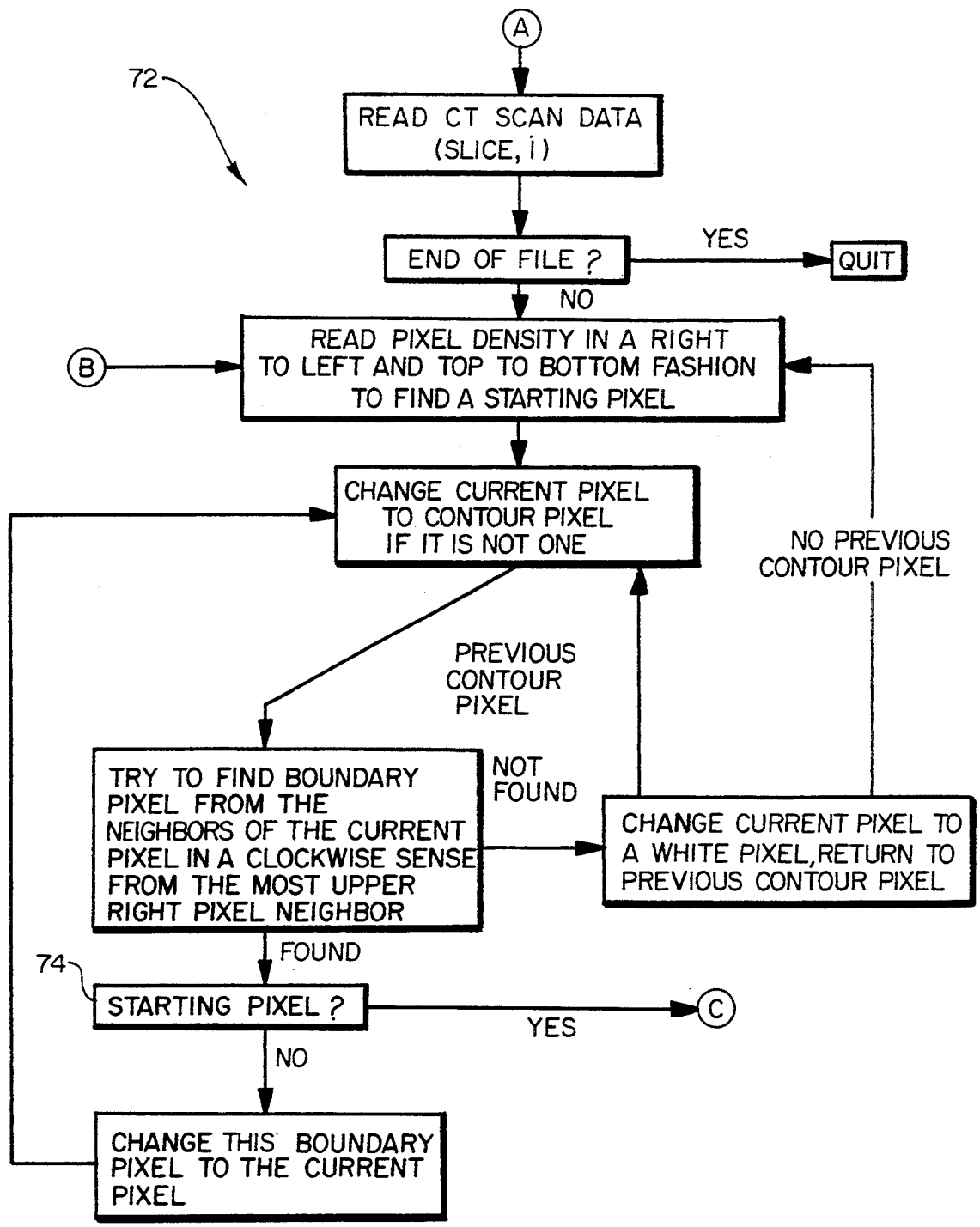
FIG. 4A is a flow chart of an outer contour deriving routine utilized during the steps of the flow chart of FIG. 3.

A preferred embodiment of the invention is illustrated in the drawings and will be described herein. FIG. 1 illustrates the components of a system wherein information pertaining to a hip joint is obtained from a CT scanner 10. The CT scan data of for instance a femur 12 in the illustrated hip joint is stored in tape memory 14 for processing bone contour information with the assistance of a bone contour deriving computer 16 in accordance with one aspect of the present invention. The bone contour information is stored in a contour tape memory 18 for processing of the information using a standard computer assisted design—computer assisted manufacturing (CAD-CAM) unit 20 (such as the aforementioned McDonnell Douglas Unigraphics CAD CAM system) and a numerically controlled milling machine 22 to provide an improved implant prosthesis 24 in accordance with another aspect of this invention.

As is well known, CT scanner 10 includes a scanning transmitter 13, and receiver 15, a scan memory 16, a disc memory 18, a reconstructor 20, and a controller 22, which are all interconnected on data bus 23. Transmitters 13 and receivers 15 may for instance be a rotating source of radiation, for example x-rays, and contain a relatively large number of radiation detectors (not shown) for detecting the amount of radiation that passes through the hip joint and femur 12 of the person being scanned, or of the scanning subject.

During operation, the scanner 10 performs a preprogramed scanning sequence which comprises a number of successive scans in linear increments of for example 5 mm apart, each successive scan being illustrated by the dotted lines in FIG. 1 representing for instance the x-rays passing through the femur 12. The transmitter and receiver are therefore rotated completely around the femur so that each dotted line in FIG. 1 represents a single scan in the scanning sequence. The transmitter and receiver are then incrementally moved a short distance, such as 5 mm along the longitudinal direction of for instance femur 12 and another scan is commenced wherein the transmitter and receiver are again rotated around the femur 12. Each scan therefore may be thought of as containing a slice of information representing the cross section of the femur.

During each scan of the scanning sequence, the output of each of the radiation detectors is continuously read and stored in the scan memory 16. Thus, for each scan, the scan memory 16 stores a set of scan data comprising a plurality of scan numbers or signals corresponding to each of the radiation detectors, the scan signals being proportional to the amount of radiation detected by the associated radiation detectors.

The scan data stored in scan memory 18 is then transmitted to reconstructor 20 for reconstruction in a conventional manner to form scan data comprising a scan number or signal associated with each X, Y portion of the scan. For example, where the image is to be displayed on a portion of a cathode ray tube (CRT) display having a width of 100 pixels and a height of 100 pixels, each X, Y portion of the scan may correspond to a respective single pixel of the CRT portion, and in this case there would be 100×100, or 10,000 signals, each of the signals being representative of the intensity of the x-rays detected by radiation detectors in receiver 15 at each of the 10,000 X, Y portions of the scan.

The scan signals stored in reconstructor 20 may be signals having a magnitude ranging from 0 to about 1400. This "reconstructor range" is based upon the well-known Hounsfield scale. The magnitude of the scan signals generated varies depending upon the type of tissue through which the x-rays pass.

As an example, reference may be made to FIG. 2 which illustrates a cross section of femur 12. FIG. 2 is a simplified illustration of the femur 12 cross section and wherein the x-ray from transmitter 13 consecutively encounters flesh 26 around the femur, cortical or hard bone 28, cancellous bone 30 closely adjacent the cortical bone, and bone marrow 32 within the interior of femur 12.

Thus, the reconstructor range or radiological density values of CT scan data representing Hounsfield numbers for flesh is generally 200 to 800; for cortical bone is generally 1100 to 1400; for cancellous bone is generally 900 to 1000; and for bone marrow is generally 200 to 800.

The scan data containing radiological density values stored in reconstructor 20 could be used to generate an image which could be displayed in a conventional manner and interpreted by the scan operator or subsequently by doctors. The displayed image represents a scan slice of femur 12 such as illustrated in the greatly simplified illustration of FIG. 2. The image is generated by displaying a particular gray-level intensity at each X, Y portion of the CRT screen, based upon the magnitude of the scan signal corresponding to that X, Y portion. The gray-level intensity displayed at each X, Y CRT portion may be simply proportional to the magnitude of scan signal generated for the corresponding X, Y scan portion.

The disc memory 18 may be used for temporary storage of scan data from scan memory 16 prior to its being reconstructed by the reconstructor 20. Reconstructed data may also be stored in disc memory 18 on a relatively long-term basis, such as days or weeks for example. In connection with the illustrated embodiment of the present invention, the reconstructed data is stored in CT scan tape memory 14 which contains the scan slice density data for the complete sequence of scan slices developed by CT scanner 10 of femur 12.

It is to be understood that CT scanner 10 and its components and operation as described above are conventional. As an example, the CT scanner may be a Model 9800 scanner commercially available from General Electric.

While FIG. 1 illustrates the inputting of CT scan slice density data from tape 14 into bone contour deriving computer 16, other forms of linkage may of course be used. For example, CT scanner 10 and computer 16 may be directly connected via a conventional data link so that scanner 12 transfers to computer 16 the sequence of scan slice density data that was produced by the CT scanner 10. In that event, the scan data transfer may take place substantially simultaneously with the scanning or it may occur at a much later time, several days or weeks later, for example.

Computer 16 may be a conventional personal computer Such as an IBM PC AT having a microprocessor, random-access memory (RAM), a read-only memory (ROM), or it may be a custom designed computer. Computer 16 is connected to a display 34 which may be a conventional (CRT) to display the scan slice images, and is connected to a contour tape memory 18 for storing femur bone contour data for each scan slice derived in accordance with one aspect of the present invention. A keyboard 36 enables the contour operator to input data into computer 16. Alternately, the contour operator may also enter data into computer 16 through the use of a light pen 38 or other data entry device.

Through the use of controller or computer 16, the contour operator develops the inner and outer bone contours of femur 12 from the sequence of scan slice density data on tape 14. For instance, referring to the simplified illustration of the femur 12 in FIG. 2, in order to form an accurate prosthesis, the physcian requires a very precise measurement of the bone surfaces defined by outer contour 40 and inner contour 44. At the present time, as indicated previously, present proposed contour deriving systems and techniques provide errors of about 8% in the derivation of inside contour 40 and outside contour 44 as compared to a hand measured value for the same contours. In contrast, using the contour deriving aspect of the present invention to form outer contour 40 and inner contour 44 of a femur, significantly reduced errors have been obtained of about 1.8% for the outer contour 40 and 2.1% for the inner contour 44. This represents significantly more accurate information available to the physician and technicians to be used for instance in the forming of an implant prosthesis.

OPERATION

Controller or computer 16 executes a program 46 as shown in the flow chart diagram of FIG. 3 to generate outer contour pixel data and inner contour pixel data for each scan slice from the scan data generated by CT scanner 10 represented on tape memory 14.

Generally, the outer and inner con, our data is generated by comparing the scan data in each scan slice containing radiological density values with certain threshold densities to ascertain whether an upper threshold density is exceeded. This indicates that the pixel having a density which exceeds the upper threshold density represents bone. However, a pixel which does not have the necessary threshold density can still be considered part of the bony contour if the rate of change of the density between it and its neighboring pixels exceeds a threshold density gradient, which is the manner in which the human eye detects contour boundaries.

The density gradient, G, is here defined to be the square root of the sum of the square of the respective densities of immediately adjacent pixels in the X and Y coordinate directions, i.e., $G = \sqrt{G_x^2 + G_y^2}$. The selection of bony pixels meeting the above criteria continues until the starting pixel has been uncountered so that the outer contour is now closed.

Once the outer contour is formed, a contour shape factor is calculated for the derived contour and a selection is made of an optimal contour based on the manner in which the calculated shape factor value changes. For the purposes of this invention, the contour shape factor is defined as the square root of the area within the contour divided by the circumference of the contour. The contour shape factor in accordance with the invention is a realization that the circumference of several derived contours will either increase significantly or significantly decrease if the contours do not follow the surface of the bone, and that in general the area within each of the derived contours remains about the same.

It has been found that the most effective contour shape factor for comparison of different formed contours is obtained by dividing the square root of the area within the contour by the circumference of the contour. Accordingly, the ratio of contour area to the contour circumference will either respectively result in a lower ratio value or a higher ratio value. Thus, when comparing a series of shape factors for consecutive contours, if the shape factor value is decreasing, this means that the circumference of the contours is increasing and that there are greater fluctuations in the contour. On the other hand, higher values of shape factor when comparing consecutive contours means that the circumference is decreasing and that there are therefore less fluctuations in the contour. Therefore, in accordance with the present invention, there is derived a manner in which the selection of an optimal contour is obtained based on the manner in which the shape factor value changes. Specifically, increasing values of shape factor are desired as this represents the most accurate representation of the bone contour. Other shape factor techniques may be utilized to select the optimal contour, such as changes in chord length, changes in tangential slopes, or other geometrical factors.

Following the determination of the outer contour pixel data for an optimum contour in each scan slice, the inner contour is formed and the inner contour pixel data is also stored. Thus, the outer contour pixel data for outer contour 40 and the inner contour data for inner contour 44 as shown in FIG. 2 is stored in contour tape memory 18 so that a more precise implant prosthesis can be derived in accordance with conventional techniques for directing NC cutting machines. The specific manner in which this more accurate contour formation is accomplished in accordance with the present invention is described in detail below.

A flow chart of the computer program 46 is shown in FIG. 3. This flow chart describes the operation of the system after for instance the CT scan data on tape 14 has been entered into computer 16 and the contour operator has selected a particular scan slice for which the outer contour 40 and inner contour 44 data is to be derived. A selected CT scan slice with the derived outer and inner contour in accordance with program 46 is displayed on display 34 so that the contour operator can insure that realistic and accurate results are obtained. In certain instances, the contour operator must use light pen or cursor 38 to redirect the developed contour from a point of undesired deviation. Starting in step 48, the program directs the reading of pixel density from for instance the upper righthand corner of the scan slice data and continuing in a line by line manner until the last line of scan sliced data is reached at the bottom left corner of the scan slice. In step 50, the pixel density gradient with respect to immediately neighboring pixels is calculated using the density gradient relationship described previously. In step 52, it is determined whether the pixel under investigation satisfies the density threshold and the density gradient threshold using the first level of threshold values from a density lookup table illustrated in FIG. 7.

Referring to FIG. 7, the first line of the lookup table shows that the lower threshold and the upper threshold of density value of 1400 corresponds to that of a pixel being in bone. Also, the density gradient threshold for this first level in the lookup table is zero indicating that any pixel will be selected which exceeds the threshold density of 1400 signifying that the first search is for any bone pixel.

When such a bone pixel has been located, step 54 begins a reading of the density and a calculating of the density gradient of neighboring pixels to the initial starting pixel and a continued acceptance through step 56 of pixels meeting the requirement of the first line of the density lookup table of FIG. 7 until a closed loop contour has been achieved by returning to the starting pixel with at least 50 pixels having been found as shown in step 58. Step 60 indicates that a proposed outer contour of at least 50 pixels has been derived.

In accordance with the present invention, a shape factor routine is initiated in steps 62, 64 and 66 to compare proposed formed contours and to select the optimum contour according to the shape factor value in accordance with this invention.

Thus, in general, the proposed formed contour in step 60 is used to calculate a contour shape factor in step 62 and to compare the shape factor value with prior contour shape factor values in step 64. After the first outer contour has been formed, then the next density and density gradient threshold levels are selected from density lookup table 65 via step 66 and another contour is formed in the same manner as the previous steps. When an increased value is obtained for the shape factor in comparing the shape factor value of a sequence of contours, then the optimum contour is selected and the outer contour pixel data for that scan slice is stored in accordance with step 68. If the shape factor value was not satisfactory, step 68 would be initiated to again select the next threshold levels in density lookup table 65 to derive further proposed contours.

After the formation of the outer contour 40 for the scan slice, the inner contour 44 is formed and this data is stored for that scan slice in accordance with step 70.

Once the outer contour data and the inner contour data have been developed for a scan slice, this information may be stored in tape 18 or may be directly transferred through standard communication links to a CAD-CAM unit 20.

Referring now to FIG. 4A there is illustrated the details of an outer contour routine 72 which represents the detailed program steps of controller or computer 16 for deriving outer contour 40 and which steps are shown generally in FIG. 3 as steps 48-60. Thus, once the starting pixel has been found which means that the contour loop has been closed, shown in step 74, this corresponds to step 60 in FIG. 3. Similarly, the shape factor routine shown generally in steps 62, 64 and 66 of FIG. 3 is shown in more detailed steps in shape factor routine 76 of FIG. 4B which operates in conjunction with the outer contour routine of FIG. 4A.

Figure 4B:
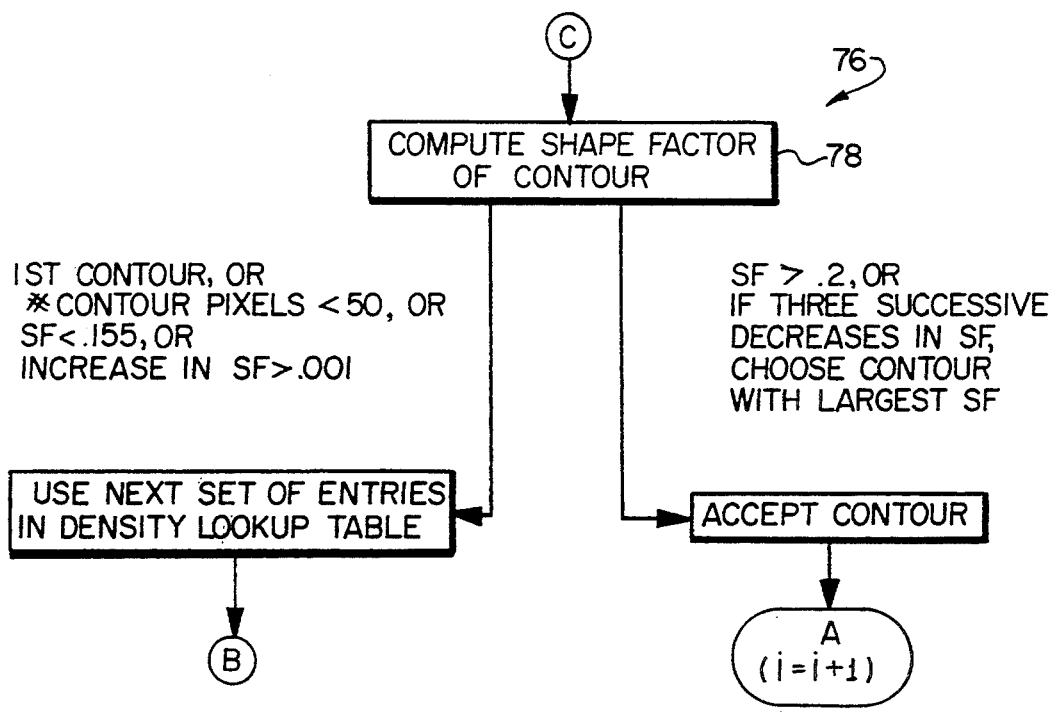
FIG. 4B is a flow chart of a contour shape factor routine utilized during the steps of the flow chart of FIG. 3.

The various terms used in the detailed routines of FIGS. 4A and 4B are defined as follows:

A "black pixel" satisfies one of the following criteria:
(1) density greater than or equal to upper threshold, or
(2) density less than upper threshold but greater than lower threshold, and average of X and Y density gradients greater than density gradient threshold.

A "white pixel" is a pixel which is not black.

A "boundary pixel" satisfies both of the following criteria:
(1) must be a black pixel, and
(2) at least one of its eight neighboring pixels must be a white pixel.

A "starting pixel" is the first pixel on each CT slice that satisfies both of the following criteria:
(1) must be a boundary pixel, and
(2) at least two of its eight neighboring pixels are boundary pixels.

A contour pixel is a boundary pixel that has been determined to lie on the contour.

The density lookup table 65 contains a repetitive listing of lower and upper density threshold and the density gradient threshold values. Each set of density values are arranged with a decreasing value for the lower density and upper density threshold.

As illustrated on FIG. 4B, if the result of the computation of the shape factor of a contour in step 78 results in a shape factor value greater than 0.2, or if three successive decreases in the shape factor value are obtained, then the contour is chosen with the largest shape factor.

Figure 5B:
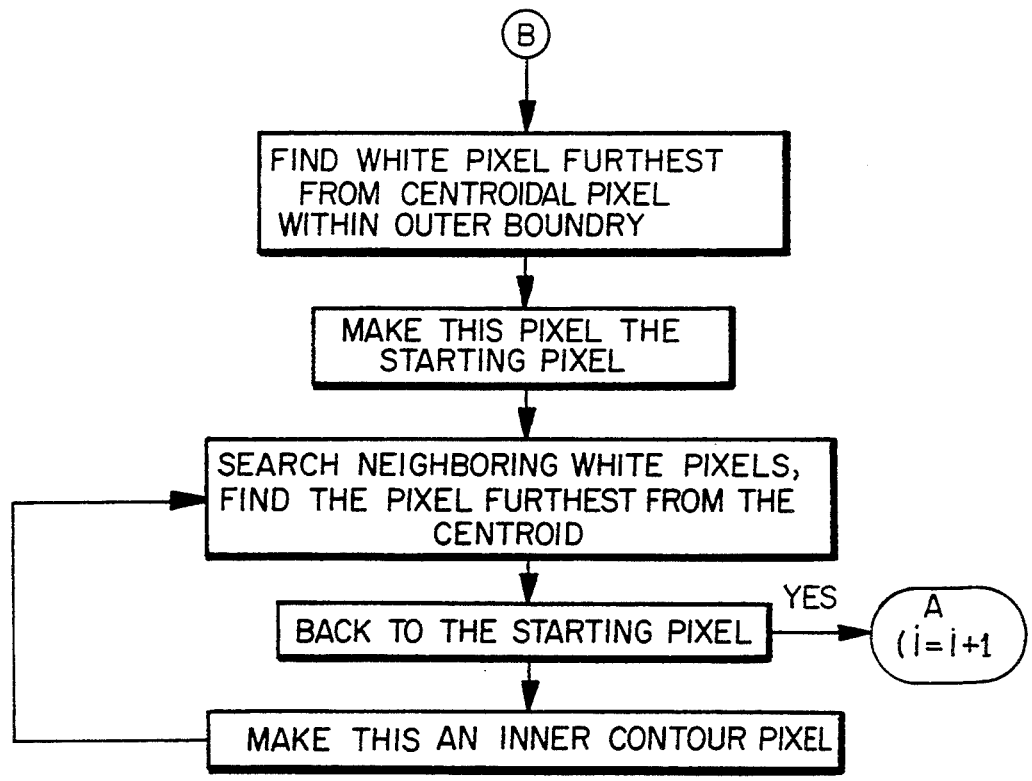
FIG. 5B is a flow chart continuing the inner contour routine of FIG. 5A.

With reference to FIGS. 5A and 5B, there is illustrated an inner contour routine 80 with detailed program steps corresponding to the general illustration of step 70 in FIG. 3. The terms used in inner contour routine 80 shown in FIGS. 5A and 5B are defined as follows:

A "black pixel" satisfies both of the following criteria:
(1) density>dynamic threshold
(2) the pixel is inside the contour boundary.

A "white pixel" is a pixel which is not black.

"Dynamic threshold" is a density threshold which is altered based on the density of surrounding pixels.

The steps of inner contour routine 80 are involved with the comparing of pixel density values within the inner contour 40 using changing density thresholds in a dynamic manner and constantly looking for bone pixels, i.e., pixels of high density such as around 1400 values.

Referring to FIG. 6, there is illustrated a smoothing routine 82 for eliminating high points or large deviations in the inner surface contour for each scan slice. Such smoothing routines are well-known and others may be desired rather than the smoothing routine shown in FIG. 6. In addition, the contour operator may manually smooth the inner surface contour in each scan data slice through the use of light pen or cursor 38.

In accordance with the principles of the present invention, a prosthesis may be formed from the derived outer and inner contour information such that a custom total hip design can be provided. Because the errors in deriving a contour have been significantly reduced in accordance with the present invention, errors in linear measurements, which are of particular significance for custom total hip design, are accordingly greatly reduced. Thus, the use of the present invention to derive outer and inner contour information is accurate enough for contouring in custom total hip design.

The foregoing detailed description has been given for clearness of understanding only, and no unnecessary limitations should be understood therefrom, as modifications will be obvious to those skilled in the art.

What is claimed is:

1. Computer controlled apparatus for developing bone contour data of a bone structure internal to a body comprising:

CT scanner means for developing CT scan data corresponding to the bone structure and surrounding tissue, said CT scan data including radiological density values for discrete points of said bone structure and surrounding tissue in each scan of said CT scan data;

memory means for storing said developed CT scan data;

first computer means for using said stored CT scan data and deriving a radiological density gradient value for said discrete points with respect to neighboring points in each scan;

second computer means for deriving the contour of said outer surface of the bone structure using the radiological density values and the radiological density gradient values and developing bone outer contour data;

comparison means for comparing the changes in contour circumference and area defining a contour shape factor of consecutively derived contours of said outer surface;

selection means for selecting a derived contour of said outer surface having a higher value of contour shape factor corresponding to a more accurately derived contour; and third computer means for deriving the contour of said inner surface of the bone structure using said developed bone outer contour data and said density values and developing bone inner contour data.

* * * * *